United States Patent
Doi et al.

(10) Patent No.: US 7,241,916 B2
(45) Date of Patent: Jul. 10, 2007

(54) PROCESS FOR PRODUCING METHACRYLIC ESTER

(75) Inventors: Junichi Doi, Hiroshima (JP); Yoshihiko Satou, Hiroshima (JP); Yoshiyuki Taniguchi, Hiroshima (JP); Masanori Tokuda, Tokyo (JP)

(73) Assignee: Mitsubishi Rayon Co., Ltd., Tokyo (JP)

(*) Notice: Subject to any disclaimer, the term of this patent is extended or adjusted under 35 U.S.C. 154(b) by 28 days.

(21) Appl. No.: 10/540,924

(22) PCT Filed: Feb. 3, 2004

(86) PCT No.: PCT/JP2004/001036

§ 371 (c)(1),
(2), (4) Date: Jun. 29, 2005

(87) PCT Pub. No.: WO2004/069783

PCT Pub. Date: Aug. 19, 2004

(65) Prior Publication Data

US 2006/0084823 A1  Apr. 20, 2006

(30) Foreign Application Priority Data

Feb. 7, 2003  (JP)  ............................. 2003-030671

(51) Int. Cl.
*C07C 67/02* (2006.01)

(52) U.S. Cl. .................................................... 560/217
(58) Field of Classification Search .................... None
See application file for complete search history.

(56) References Cited

U.S. PATENT DOCUMENTS 5,037,978 A * 8/1991 Mirabelli .................... 544/171

FOREIGN PATENT DOCUMENTS

| EP | 0 968 995 | 1/2000 |
|---|---|---|
| JP | 55-087747 | 7/1980 |
| JP | 63-115850 | 5/1988 |
| JP | 03-118352 | 5/1991 |
| JP | 2000-16966 | 1/2000 |

* cited by examiner

*Primary Examiner*—Thurman K. Page
*Assistant Examiner*—Yevgeny Valenrod
(74) *Attorney, Agent, or Firm*—Oblon, Spivak, McClelland, Maier & Neustadt, P.C.

(57) ABSTRACT

A method of producing a methacrylic acid ester which comprises carrying out an ester-exchange reaction between methyl methacrylate and an alcohol or a phenol while removing by-product methanol as an azeotropic mixture with methyl methacrylate from the reaction system under reflux conditions, by the use of a reaction apparatus equipped with a distillation column. A methacrylic acid ester is produced with a good productivity by controlling the reflux ratio.

10 Claims, No Drawings

PROCESS FOR PRODUCING METHACRYLIC ESTER

TECHNICAL FIELD

The present invention relates to a method of producing a methacrylic acid ester (inclusive of a phenolic ester).

BACKGROUND ART

Heretofore, a methacrylic acid ester is industrially produced by an esterification reaction between a methacrylic acid and an alcohol or a phenol in the presence of an acid catalyst, or by an ester-exchange reaction between a methacrylic acid ester and an alcohol or a phenol in the presence of an ester-exchange catalyst. In recent years, the method of producing the methacrylic acid ester by the ester-exchange reaction is often used, because both of a starting material and a product are an ester and an alcohol or a phenol, and hence, the products are relatively easily separated by distillation and waste water is not generated.

As the ester-exchange reaction, a reaction using methyl methacrylate as shown in the following formula (1) is frequently employed:

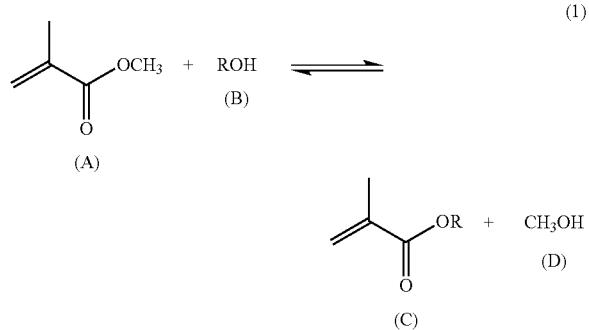

(1)

wherein R represents an alkyl group, an aryl group, an alkenyl group, or an aralkyl group.

However, the ester-exchange reaction shown by the above formula (1) is an equilibrium reaction, and hence, it does not proceed beyond a certain conversion. When the conversion is low, it is necessary to separate all the ingredients of a raw methyl methacrylate (A), a raw alcohol (B), an end product methacrylic acid ester (C), and by-product methanol (D) after the reaction, which makes the operations complicated.

Therefore, in order to shift the equilibrium to the product side and further enhance the conversion, it is conducted to remove by-product methanol (D) together with an azeotropic solvent from the reaction system. For example, since raw methyl methacrylate (A) forms an azeotropic mixture with by-product methanol (D), a charge mole number of raw methyl methacrylate (A) is set so as to be in excess of a charge mole number of the raw alcohol (B), and by-product methanol (D) is removed as an azeotropic mixture with methyl methacrylate (A) from the reaction system.

However, in a case where the reaction rate, i.e., the production rate of by-product methanol (D) is not sufficiently high, a large excess of methyl methacrylate (A) is necessary to remove by-product methanol (D), so that the productivity tends to be poor.

Accordingly, in order to form an azeotropic mixture in which a concentration of by-product methanol (D) is enhanced and to remove it from the reaction system, there is employed a method wherein a portion of the azeotropic mixture is distilled out and the remainder is refluxed while controlling a reflux ratio, by the use of a distillation column. In this method, it is desired to produce the methacrylic acid ester with a higher productivity.

For example, Japanese Patent Laid-Open Nos. 87747/1980, 115850/88 and 118352/1991 contain processes for producing an intended methacrylic acid ester by an ester-exchange reaction between methyl methacrylate and an alcohol or a phenol by the use of a reactor equipped with a distillation column, wherein the ester-exchange reaction is carried out while extracting an azeotropic mixture of methyl methacrylate and methanol under the control of only a column top temperature of the distillation column.

DISCLOSURE OF THE INVENTION

An object of the present invention is to provide a method of producing a methacrylic acid ester which comprises the step of carrying out an ester-exchange reaction between methyl methacrylate and the alcohol or the phenol while removing by-product methanol as an azeotropic mixture with methyl methacrylate from the reaction system under reflux conditions, wherein the methacrylic acid ester is produced with a good productivity by controlling the reflux ratio.

The present invention relates to a method of producing a methacrylic acid ester of an alcohol or a phenol which comprises the step of carrying out an ester-exchange reaction between methyl methacrylate and the alcohol or the phenol while removing by-product methanol as an azeotropic mixture with methyl methacrylate from the reaction system via a distillation column under reflux conditions, by the use of a reaction apparatus equipped with the distillation column, wherein the reaction is carried out while controlling the reflux ratio so that a temperature of the uppermost stage in the distillation column may be from 63 to 68° C., a temperature of the middle stage in the distillation column may be from 68 to 90° C., and a temperature of the lowest stage in the distillation column may be from 90 to 100° C. in terms of the temperatures at normal pressure, while the conversion of the alcohol or the phenol is within the range of 10 to 90%.

Moreover, the present invention relates to a method of producing a methacrylic acid ester of an alcohol or a phenol which comprises the step of carrying out an ester-exchange reaction between methyl methacrylate and the alcohol or the phenol while removing by-product methanol as an azeotropic mixture with methyl methacrylate from the reaction system via a distillation column under reflux conditions, by the use of a reaction apparatus equipped with the distillation column, wherein the removal of the azeotropic mixture of methanol and methyl methacrylate from the reaction system is started after a temperature of the uppermost stage in the distillation column has reached from 63 to 68° C., a temperature of the middle stage in the distillation column has reached from 68 to 90° C., and a temperature of the lowest stage in the distillation column has reached from 90 to 100° C. in terms of the temperatures at normal pressure; and the reaction is carried out while controlling the reflux ratio so that the temperatures in the distillation column may be maintained within the above range, while the conversion of the alcohol or the phenol is within the range of 10 to 90%.

Moreover, the present invention relates to the above-mentioned method of producing a methacrylic acid ester, wherein, after the conversion of the alcohol or the phenol has exceeded 97%, by-product methanol is completely removed as an azeotropic mixture with methyl methacrylate from the reaction system while controlling the reflux ratio so that a temperature of the uppermost stage in the distillation column may be 95° C. or higher, and temperatures of the middle stage and the lowest stage in the distillation column may be 99° C. or higher in terms of the temperatures at normal pressure, and the reaction is terminated.

The term "reflux ratio" herein means a ratio of a refluxed amount to a distilled amount of a condensed liquid, in a case where a portion of the condensed liquid is distilled out and the remainder is refluxed after a vapor evaporated from the inside of a reactor of a reaction apparatus goes through a distillation column and is condensed in a condenser.

Moreover, when the distillation column is operated at a pressure other than normal pressure (atmospheric pressure), a way of converting a temperature in the distillation column into a temperature at normal pressure is as follows.

First, a liquid composition of a mixed solution of methanol and methyl methacrylate whose boiling point at the pressure (the operating pressure of the distillation column) is an actual temperature in the distillation column, is obtained from the boiling point-composition diagram at the above pressure.

Next, a boiling point of the mixed solution of methanol and methyl methacrylate having the liquid composition at normal pressure is obtained from the boiling point-composition diagram at normal pressure, and the thus obtained boiling point is defined as "the temperature at normal pressure".

In the present invention, the reflux ratio is controlled so that the temperatures in the distillation column may be within the above range, whereby the methacrylic acid ester, which is the end product, can be produced with a good productivity.

When the reflux ratio is excessively increased, an efficiency of removing by-product methanol from the reaction system deteriorates, and the methanol concentration in the whole distillation column rises more than necessary, which brings about even the rise of the methanol concentration in the reactor in a certain case. As a result, it becomes difficult to shift the equilibrium reaction to the product side. On the other hand, when the reflux ratio is excessively decreased, the methanol concentration in the azeotropic mixture which is removed from the reaction system lowers, and in consequence, methyl methacrylate is removed from the reaction system more than necessary. As a result, in a case where a charge amount of methyl methacrylate is too small, all of methyl methacrylate is distilled off before the desired conversion has been reached, and hence, the reaction does not proceed any more. The production rate of by-product methanol varies depending on various factors such as a molar ratio of the starting materials and a catalyst to be used. However, according to the present invention, by-product methanol can be removed from the reaction system efficiently and in a state where the methanol concentration in the azeotropic mixture with methyl methacrylate is sufficiently raised.

BEST MODE FOR CARRYING OUT THE INVENTION

A raw alcohol or phenol may be suitably determined in accordance with an aimed methacrylic acid ester. Specific examples of the raw alcohol or phenol include aliphatic saturated alcohols such as methanol, ethanol, n-propanol, i-propanol, n-butanol, i-butanol, t-butanol, n-pentanol, t-amyl alcohol, n-hexanol, n-heptanol, n-octanol, 2-ethylhexyl alcohol, n-nonanol, n-decanol, n-undecanol, n-dodecanol, lauryl alcohol, stearyl alcohol, ethylene glycol, 1,3-propanediol, 1,2-propanediol, 1,4-butanediol, 1,5-pentanediol, 1,6-hexanediol, 1,8-octanediol, 1,9-nonanediol, 1,10-decanediol, 1,12-dodecanediol and glycerol; aliphatic unsaturated alcohols such as allyl alcohol, 1,1-dimethylallyl alcohol, prenol and isoprenol; aliphatic cyclic alcohols such as cyclohexanol, methylcyclohexanol, cyclohexane-1,4-dimethanol, norbornane-2-methanol, 5-norbornene-2-methanol, 1-adamantanol and 2-methyl-2-adamantanol; functional group-containing alcohols such as glycidol, isopropylideneglycerol and glycerin carbonate; phenols such as phenol and 2-phenylphenol; and aryl group-containing alcohols such as benzyl alcohol, 1-phenylethyl alcohol and 2-phenylethyl alcohol.

A charge/mixing ratio between the raw methyl methacrylate and the raw alcohol or phenol may be suitably determined in accordance with the starting materials and a catalyst which are used. Usually, an amount of methyl methacrylate to be used is preferably 1.2 mole or more per mole of the alcohol or phenol, and it is preferably 20 mole or less per mole of the alcohol or phenol. In this connection, when the starting material is a polyhydric alcohol, the amount of methyl methacrylate to be used is preferably an amount obtained by multiplying the above value by the valence of the polyhydric alcohol.

In the present invention, methyl methacrylate and the alcohol or phenol are usually reacted with each other in the presence of a catalyst.

The catalyst to be used in the present invention is not particularly limited, and any catalyst can be used so long as it has an ester-exchange activity. Examples of the catalyst include titanium compounds such as tetramethyl titanate, tetraisopropyl titanate, tetra-n-butyl titanate, tetra-2-ethylhexyl titanate and tetrastearyl titanate; tin compounds such as dibutyltin oxide, dioctyltin oxide, dimethyltin dimethoxide, dibutyltin dimethoxide, dibutyltin dimethacrylate, tetrabutyl-diacetoxydistannoxane, tetrabutyl-dimethacryloyloxydistannoxane, tetrabutyl-diacryloyloxydistannoxane, tetraoctyl-dimethacryloyloxydistannoxane and tetraoctyl-diacryloyloxydistannoxane; carbonates of alkali metals and alkaline earth metals such as potassium carbonate, sodium carbonate, magnesium carbonate, calcium carbonate and lithium carbonate; chlorides of alkali metals and alkaline earth metals such as calcium chloride, sodium chloride, magnesium chloride, potassium chloride and lithium chloride; hydroxides of alkali metals and alkaline earth metals such as sodium hydroxide, potassium hydroxide, lithium hydroxide, magnesium hydroxide and calcium hydroxide; and metal alkoxides such as aluminum isopropoxide and sodium methoxide. The catalysts may be used singly or in combination of two or more of them.

An amount of the catalyst to be used may be suitably determined in accordance with the starting materials and the catalyst which are used. Usually, an amount of the catalyst to be used is preferably 0.0001 mole or more per mole of the alcohol or phenol, and it is preferably 0.2 mole or less per mole of the alcohol or phenol.

In the present invention, for the purpose of inhibiting the polymerization of the methacrylic acid ester, it is preferable to carry out the ester-exchange reaction in a state where a polymerization inhibitor is added into a reactor. In addition, since methyl methacrylate is also present in the distillation column, it is preferable to supply a polymerization inhibitor to the whole distillation column for the purpose of inhibiting the polymerization, as in the reactor. Specifically, a polymerization inhibitor may be dissolved in methyl methacrylate, and the resultant solution may be supplied from the uppermost stage in the distillation column.

The polymerization inhibitor to be used in the present invention is not particularly limited, and any compound can be used so long as it has a polymerization-inhibiting effect to the methacrylic acid ester. Examples of the polymerization inhibitor include phenol compounds such as hydroquinone and p-methoxyphenol; amine compounds such as phenothiazine, N-phenyl-N'-isopropyl-p-phenylenediamine, N,N'-di-2-naphthyl-p-phenylenediamine and N-phenyl-N'-(1,3-dimethylbutyl)-p-phenylenediamine; and N-oxyl compounds such as 4-hydroxy-2,2,6,6-tetramethylpiperidine-N-oxyl, 4-benzoyloxy-2,2,6,6-tetramethylpiperidine-N-oxyl, 4-acetylamino-2,2,6,6-tetramethylpiperidine-N-oxyl and N-oxyl compounds represented by the following formula (2). The polymerization inhibitors may be used singly or in combination of two or more of them.

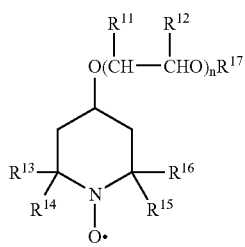

(2)

wherein both $R^{11}$ and $R^{12}$ represent a hydrogen atom, or either of $R^{11}$ or $R^{12}$ represents a hydrogen atom and the other represents a methyl group; $R^{13}$, $R^{14}$, $R^{15}$ and $R^{16}$ independently represents a linear or branched alkyl group; $R^{17}$ represents a hydrogen atom or a (meth)acryloyl group; and n is an integer of 1 to 18.

Moreover, in the present invention, for the purpose of inhibiting the polymerization of the methacrylic acid ester, an oxygen-containing gas may be supplied into the reactor or into the distillation column by air-bubbling into the reaction solution or the like.

In the present invention, a reactor of a reaction apparatus equipped with a distillation column is charged with methyl methacrylate, an alcohol or a phenol, a catalyst and a polymerization inhibitor, and the mixture is heated up to a reaction temperature to carry out an ester-exchange reaction while removing by-product methanol as an azeotropic mixture from the reaction system under reflux conditions. At this time, the removal of the azeotropic mixture of methanol and methyl methacrylate (methanol/methyl methacrylate azeotropic mixture) from the reaction system is performed by distilling a portion of the condensed liquid after a vapor evaporated from the inside of the reactor goes through the distillation column and is condensed in a condenser.

The distillation column to be used in the present invention is not particularly limited, and examples thereof include a packed column which is packed with a filler such as helipacks, McMahons or cascade mini-rings, and tray-type columns such as an Oldershaw column and a lift-tray.

In view of a separation ability, the number of theoretical stages of the distillation column is preferably five stages or more, more preferably ten stages or more. Moreover, in that a pressure difference is suppressed to a low level, the number of theoretical stages of the distillation column is preferably fifty stages or less, more preferably thirty stages or less.

The ester-exchange reaction is carried out at normal pressure, reduced pressure or slightly increased pressure. Specifically, a pressure of 6600 to 202000 Pa is preferable.

The reaction temperature (temperature in the reactor) may be suitably determined, but in the case of carrying out the reaction at normal pressure, a temperature of 100 to 150° C. is usually preferable.

In the present invention, since methanol, which is formed as a by-product in the reaction, is removed azeotropically together with methyl methacrylate, methyl methacrylate is used in an excess amount relative to the alcohol or the phenol as described above. After the reactor has been charged with the starting materials, the mixture is heated up to the reaction temperature so as to be in a reflux state. At this time, since methyl methacrylate is excessively used, methyl methacrylate is mainly distributed in the distillation column at an early stage of the reaction. When methanol is formed together with a methacrylic acid ester as the ester-exchange reaction proceeds, by-product methanol azeotropically boils together with methyl methacrylate and ascends through the distillation column. The azeotropic temperature of methanol/methyl methacrylate at normal pressure is 64° C., and the azeotropic composition is methanol/methyl methacrylate of 91/9 by weight. When the composition at the uppermost stage in the distillation column is made to be the azeotropic composition of methanol/methyl methacrylate and this is removed from the reaction system, the distilled amount of methyl methacrylate can be suppressed to a low level. Moreover, there is a risk that the temperature control only at the uppermost stage may result in the deviation from the azeotropic composition. Therefore, from the viewpoint of more stable operation, it is preferable to control the temperatures of the middle stage and the lowest stage in the distillation column.

In the present invention, the temperature of the uppermost stage (the theoretical stage in the case of the packed column) in the distillation column is made within the range of 63 to 68° C. in terms of the temperature at normal pressure, while the conversion of the alcohol or the phenol is within the range of 10 to 90%, preferably 5 to 95%, particularly preferably 4 to 97%. The temperature of the uppermost stage in the distillation column is preferably from 63 to 65° C. in terms of the temperature at normal pressure. The temperature is a temperature close to the azeotropic temperature of methanol and methyl methacrylate at normal pressure. By making the temperature of the uppermost stage in the distillation column within the above range, an azeotropic mixture having a high methanol concentration is removed from the reaction system, and hence, the distilled amount of methyl methacrylate can be suppressed to a low level. As a result, the charge amount of the raw methyl methacrylate (mixing ratio relative to the raw alcohol or phenol) can be reduced, and consequently, the productivity can be improved.

The temperature of the middle stage in the distillation column is made within the range of 68 to 90° C. in terms of the temperature at normal pressure, while the conversion of the alcohol or the phenol is within the range of 10 to 90%, preferably 5 to 95%, particularly preferably 4 to 97%. The temperature of the middle stage in the distillation column is preferably 70° C. or higher in terms of the temperature at normal pressure, and is preferably 80° C. or lower in terms of the temperature at normal pressure. When the temperature of the middle stage in the distillation column is too low, methanol may reach the lowest stage in the distillation column and return to the inside of the reactor, so that the concentration of methanol in the reactor increases and thereby the progress of the ester-exchange reaction is inhibited in some cases. In addition, when the temperature of the middle stage in the distillation column is too high, the composition at the uppermost stage in the distillation column tends to deviate from the azeotropic composition and there is a risk of increasing the distilled amount of methyl methacrylate.

It is to be noted that the middle stage in the distillation column means the stage (the theoretical stage in the case of the packed column) at a position of half (which is obtained by rounding up fractions below decimal point) of the total stages as counted from the uppermost stage (the theoretical stage in the case of the packed column).

The temperature of the lowest stage (the theoretical stage in the case of the packed column) in the distillation column is made within the range of 90 to 100° C. in terms of the temperature at normal pressure, while the conversion of the alcohol or the phenol is within the range of 10 to 90%, preferably 5 to 95%, particularly preferably 4 to 97%. The temperature of the lowest stage in the distillation column is preferably from 99 to 100° C. in terms of the temperature at normal pressure. By making the temperature of the lowest stage in the distillation column within the above range, the content of methanol is reduced, and the return of methanol into the reactor can be prevented.

By carrying out the ester-exchange reaction with maintaining the temperatures in the distillation column within the above ranges by controlling the reflux ratio, while removing the azeotropic mixture of methanol/methyl methacrylate from the reaction system, it is possible to operate the apparatus efficiently and stably with minimizing the loss of methyl methacrylate especially when the conversion of the alcohol or the phenol is within the range of 4 to 97%.

Moreover, in the present invention, in view of reducing the loss of methyl methacrylate, it is preferable that the apparatus is operated in a total reflux state until the temperatures reach the above ranges, and, after the temperatures have reached the ranges, the removal of the azeotropic mixture of methanol/methyl methacrylate from the reaction system is started.

On the other hand, though the situation varies depending on the kinds and the amounts of the raw alcohol and the catalyst, and the like, the production rate of methanol decreases, and thus methanol does not ascend from the reactor to the distillation column when the conversion of the alcohol or the phenol exceeds 97%. Therefore, the temperature begins to rise from the lowest stage in the distillation column.

In the present invention, for terminating the reaction after the conversion of the alcohol or the phenol has exceeded 97%, it is preferable to remove by-product methanol as the azeotropic mixture with methyl methacrylate from the reaction system completely, while controlling the reflux ratio so that a temperature of the uppermost stage in the distillation column may be 95° C. or higher, and temperatures of the middle stage and the lowest stage in the distillation column may be 99° C. or higher in terms of the temperatures at normal pressure. As the method of removing the methanol present in the distillation column from the reaction system completely, there may be mentioned, for example, a method of decreasing the reflux ratio gradually and increasing the distilling ratio, or a method of removing all the condensed liquid circulating through the condenser and the reflux line out of the reaction system from the upper stage in the distillation column by setting the reflux ratio to 0, i.e., by distilling all.

The complete removal of methanol remaining in the reaction system, e.g., in the distillation column and in the reflux line, by the above methods can prevent the return of the remaining methanol from the distillation column to the inside of the reactor after the termination of the reaction and the subsequent shift of the equilibrium reaction to the starting material side to thereby lower the conversion.

EXAMPLES

Hereinafter, the present invention will be concretely described with reference to the following examples, but the present invention is not limited to these examples.

In the examples and comparative examples, analyses were carried out by gas chromatography.

The yield and the conversion were calculated as follows:

Yield (%)=$A/B$×100

Conversion (%)=$(B-C)/B$×100 wherein A represents a mole number of an obtained end product, B represents a charge mole number of an alcohol or a phenol, and C represents a mole number of the unreacted alcohol or phenol.

Moreover, a composition of an azeotropic mixture of methanol/methyl methacrylate and a composition of a reaction solution were calculated as follows:

Content of a target compound (%)=$D/E$×100 wherein D represents a weight of the target compound, and E represents the total weight of all the compounds.

Example 1

As a reaction apparatus, there was used a 3 liter four-neck flask (reactor) equipped with a 20 stages Oldershaw distillation column. This apparatus was set up so that a vapor which ascended to the distillation column by heat was cooled in the condenser and returned to the uppermost stage in the distillation column through the reflux line.

First, the reactor was charged with 1051.3 g (10.5 mol) of methyl methacrylate, 652.2 g (3.5 mol) of lauryl alcohol and 0.04 g of 4-acetylamino-2,2,6,6-tetramethylpiperidine-N-oxyl, and the mixture was then heated to conduct dehydration in the reaction system over a period of 1 hour under the total reflux. Then, the reactor was cooled and charged with 0.86 g (0.0035 mol) of tetramethyl titanate (purity: 70%), and heating was begun again. While continuously supplying a solution having a concentration of 1000 ppm obtained by dissolving 4-acetylamino-2,2,6,6-tetramethylpiperidine-N-oxyl in methyl methacrylate at 2 ml/hr from the uppermost stage in the distillation column and while introducing air into the reaction solution at 20 ml/min, the ester-exchange reaction was carried out at normal pressure with maintaining the temperature in the reactor at 111 to 129° C. During the reaction, the reaction solution in the reactor was sampled and the samples were analyzed by gas chromatography to determine the conversion with time.

At the beginning of the reaction, the operation was conducted under the total reflux, and the removal of an azeotropic mixture of methanol/methyl methacrylate from the reaction system was started at the time when the temperature of the uppermost stage in the distillation column reached 64° C., the temperature of the middle stage 71° C., and the temperature of the lowest stage 100° C. (the conversion of 4% at this time). Thereafter, until the conversion reached 97%, the reaction was carried out while controlling the reflux ratio within the range of 5 to 50, so as to maintain the temperature of the uppermost stage in the distillation column at 64 to 65° C., the temperature of the middle stage at 70 to 80° C., and the temperature of the lowest stage at 99 to 100° C.

After 3 hours from the beginning of the reaction, the conversion reached 97% and the temperature of the middle stage in the distillation column rose to 88° C. Thereafter, the reflux ratio was gradually lowered to 0.1 and the temperatures of the uppermost stage and the middle stage in the distillation column were raised up to 99° C.

Then, in order to completely remove, from the reaction system, methanol contained in the liquid refluxed from the uppermost stage in the distillation column to the uppermost stage in the distillation column again through the condenser and the reflux line, the reflux ratio was set to zero, and thereby all the liquid in the reflux line was distilled off until the temperature of the uppermost stage in the distillation column was stably maintained at 97° C. or higher. Thus, the reaction was terminated. The reaction time was 4 hours. During this time, the temperature of the uppermost stage in the distillation column was maintained at 95° C. or higher, and the temperatures of the middle stage and the lowest stage in the distillation column were maintained at 99° C. or higher.

The amount of the azeotropic mixture of methanol/methyl methacrylate removed was 215.2 g, and the content of methanol was 52.2% (112.3 g) and the content of methyl methacrylate was 47.5% (102.2 g).

When 1485.8 g of the resulting reaction solution in the reactor was analyzed by gas chromatography, it contained 40.1% of methyl methacrylate, 0.13% of lauryl alcohol and 59.0% of lauryl methacrylate, and the yield was 98.4%.

Example 2

The same reaction apparatus as used in Example 1 was used.

First, the reactor was charged with 750.9 g (7.5 mol) of methyl methacrylate, 676.3 g (2.5 mol) of stearyl alcohol and 0.042 g of 4-acetylamino-2,2,6,6-tetramethylpiperidine-N-oxyl, and the mixture was then heated to conduct dehydration in the reaction system over a period of 1 hour under the total reflux. Then, the reactor was cooled and charged with 1.23 g (0.005 mol) of tetramethyl titanate (purity: 70%), and heating was begun again. And thereafter, the ester-exchange reaction was carried out in the same manner as in Example 1.

At the beginning of the reaction, the operation was conducted under the total reflux, and the removal of an azeotropic mixture of methanol/methyl methacrylate from the reaction system was started at the time when the temperature of the uppermost stage in the distillation column reached 64.5° C., the temperature of the middle stage 74° C., and the temperature of the lowest stage 98.8° C. (the conversion of 4% at this time). Thereafter, until the conversion reached 97%, the reaction was carried out while controlling the reflux ratio within the range of 5 to 50, so as to maintain the temperature of the uppermost stage in the distillation column at 64 to 65° C., the temperature of the middle stage at 70 to 80° C., and the temperature of the lowest stage at 99 to 100° C.

After 4 hours from the beginning of the reaction, the conversion reached 98% and the temperature of the middle stage in the distillation column rose to 93° C. Thereafter, in order to completely remove, from the reaction system, methanol contained in the liquid refluxed from the uppermost stage in the distillation column to the uppermost stage in the distillation column again through the condenser and the reflux line, the reflux ratio was set to zero, and thereby all the liquid in the reflux line was distilled off until the temperature of the uppermost stage in the distillation column was stably maintained at 98° C. or higher. Thus, the reaction was terminated. The reaction time was 4.5 hours. During this time, the temperature of the uppermost stage in the distillation column was maintained at 95° C. or higher, and the temperatures of the middle stage and the lowest stage in the distillation column were maintained at 99° C. or higher.

The amount of the azeotropic mixture of methanol/methyl methacrylate removed was 124.5 g, and the content of methanol was 62.8% (78.2 g) and the content of methyl methacrylate was 37.2% (46.3 g).

When 1297.7 g of the resulting reaction solution in the reactor was analyzed by gas chromatography, it contained 35.0% of methyl methacrylate, 0% of stearyl alcohol and 64.8% of stearyl methacrylate, and the yield was 99.3%.

Comparative Example 1

The ester-exchange reaction was carried out in the same manner as in Example 1 except that the reflux ratio was controlled within the range of 2 to 10, so as to maintain only the temperature of the uppermost stage in the distillation column at 63 to 68° C., without controlling the temperatures of the middle stage and the lowest stage in the distillation column. As a result, the temperature of the middle stage in the distillation column became 70 to 100° C., and the concentration of methanol in the distillation column decreased and the concentration of methyl methacrylate relatively increased, so that the composition of methanol/methyl methacrylate at the column top deviates from the proper azeotropic composition (91:9), the temperature at the column top frequently became 68° C., and thus a stable operation could not be conducted.

After 4.5 hours from the beginning of the reaction, the conversion reached 97% and the temperature of the middle stage in the distillation column was 94° C. Thereafter, in order to completely remove, from the reaction system, methanol contained in the liquid refluxed from the uppermost stage in the distillation column to the uppermost stage in the distillation column again through the condenser and the reflux line, the reflux ratio was set to zero, and thereby all the liquid in the reflux line was distilled off until the temperature of the uppermost stage in the distillation column was stably maintained at 98° C. or higher. Thus, the reaction was terminated. The reaction time was 5 hours.

The amount of the azeotropic mixture of methanol/methyl methacrylate removed was 316.8 g, and the content of methanol was 35.1% (111.2 g) and the content of methyl methacrylate was 64.7% (205.0 g). Thus, a greater loss of methyl methacrylate was observed in Comparative Example 1 as compared with the case of Example 1.

When 1380.8 g of the resulting reaction solution in the reactor was analyzed by gas chromatography, it contained 36.2% of methyl methacrylate, 0.2% of lauryl alcohol and 62.9% of lauryl methacrylate, and the yield was 97.5%.

Comparative Example 2

The ester-exchange reaction was carried out in the same manner as in Comparative Example 1 except that the controlled range of the reflux ratio was changed into 10 to 100. As a result, the temperature of the uppermost stage in the distillation column was maintained at 63 to 65° C., but the temperature of the middle stage in the distillation column became 63 to 68° C., and the removing rate of methanol lowered.

After 6 hours from the beginning of the reaction, the temperature of the middle stage in the distillation column rose to 93° C. Thereafter, in order to completely remove, from the reaction system, methanol contained in the liquid refluxed from the uppermost stage in the distillation column to the uppermost stage in the distillation column again through the condenser and the reflux line, the reflux ratio was set to zero, and thereby all the liquid in the reflux line was distilled off until the temperature of the uppermost stage in the distillation column was stably maintained at 98° C. or higher. Thus, the reaction was terminated. The reaction time was 6.5 hours.

The amount of the azeotropic mixture of methanol/methyl methacrylate removed was 212.4 g, and the content of methanol was 52.5% (111.5 g) and the content of methyl methacrylate was 46.5% (98.8 g).

When 1483.4 g of the resulting reaction solution in the reactor was analyzed by gas chromatography, it contained 40.4% of methyl methacrylate, 0.13% of lauryl alcohol and 59.1% of lauryl methacrylate, and the yield was 98.5%.

In Comparative Example 2, the loss of methyl methacrylate and the yield of lauryl methacrylate were equal to those in Example 1, but the reaction time was considerably longer than that in Example 1 and thus the productivity was inferior.

Example 3

The ester-exchange reaction was carried out in the same manner as in Example 1 except that the reflux ratio was controlled within the range of 5 to 50 and the reaction was terminated with maintaining the reflux ratio of 50, which was the reflux ratio at the time when the conversion reached 97%, without distilling all. As a result, the temperature of the uppermost stage in the distillation column did not rise to 91° C. or higher and the reaction was terminated with ceasing the heating of the reactor without further operation. The reaction time was 4 hours.

The amount of the azeotropic mixture of methanol/methyl methacrylate removed was 157.7 g, and the content of methanol was 67.0% (105.7 g) and the content of methyl methacrylate was 32.8% (51.7 g).

When 1529.6 g of the resulting reaction solution in the reactor was analyzed by gas chromatography, it contained 41.7% of methyl methacrylate, 1.4% of lauryl alcohol and 55.9% of lauryl methacrylate, and the yield was 96%. In consequence, lauryl alcohol remained as much as 3.2% of the charge amount.

In Example 3, the loss of methyl methacrylate was small, but the yield slightly lowered as compared with the case of Example 1 and lauryl alcohol remained in an amount of 3.2%. This is considered to be due to the fact that methanol cannot be completely removed from the reaction system.

INDUSTRIAL APPLICABILITY

According to the present invention, a methacrylic acid ester can be produced with a good productivity by controlling the temperature of the distillation column and controlling the reflux ratio.

The invention claimed is:

1. A method of producing a methacrylic acid ester of an alcohol or a phenol which comprises carrying out an ester-exchange reaction between methyl methacrylate and the alcohol or the phenol while removing by-product methanol as an azeotropic mixture with methyl methacrylate from the reaction system via a distillation column under reflux conditions, by the use of a reaction apparatus equipped with the distillation column, wherein the reaction is carried out while controlling the reflux ratio so that the temperature of the uppermost stage in the distillation column is from 63 to 68° C., the temperature of the middle stage in the distillation column is from 68 to 90° C., and the temperature of the lowest stage in the distillation column is from 90 to 100° C. in terms of the temperatures at normal pressure, while the conversion of the alcohol or the phenol is within the range of 10 to 90%.

2. A method of producing a methacrylic acid ester of an alcohol or a phenol which comprises carrying out an ester-exchange reaction between methyl methacrylate and the alcohol or the phenol while removing by-product methanol as an azeotropic mixture with methyl methacrylate from the reaction system via a distillation column under reflux conditions, by the use of a reaction apparatus equipped with the distillation column, wherein the removal of the azeotropic mixture of methanol and methyl methacrylate from the reaction system is started after a temperature of the uppermost stage in the distillation column has reached from 63 to 68° C., a temperature of the middle stage in the distillation column has reached from 68 to 90° C., and a temperature of the lowest stage in the distillation column has reached from 90 to 100° C. in terms of the temperatures at normal pressure; and the reaction is carried out while controlling the reflux ratio so that the temperatures in the distillation column may be maintained within the above range, while the conversion of the alcohol or the phenol is within the range of 10 to 90%.

3. The method of producing a methacrylic acid ester according to claim 1, wherein, after the conversion of the alcohol or the phenol has exceeded 97%, by-product methanol is completely removed as an azeotropic mixture with methyl methacrylate from the reaction system while controlling the reflux ratio so that the temperature of the uppermost stage in the distillation column is 95° C. or higher, and temperatures of the middle stage and the lowest stage in the distillation column are 99° C. or higher in terms of the temperatures at normal pressure, and the reaction is terminated.

4. The method of producing a methacrylic acid ester according to claim 2, wherein, after the conversion of the alcohol or the phenol has exceeded 97%, by-product methanol is completely removed as an azeotropic mixture with methyl methacrylate from the reaction system while controlling the reflux ratio so that the temperature of the uppermost stage in the distillation column is 95° C. or higher, and temperatures of the middle stage and the lowest stage in the distillation column are 99° C. or higher in terms of the temperatures at normal pressure, and the reaction is terminated.

5. The method of producing a methacrylic acid ester according to claim 1, wherein the conversion of the alcohol or the phenol is within the range of 5-95%.

6. The method of producing a methacrylic acid ester according to claim 2, wherein the conversion of the alcohol or the phenol is within the range of 5-95%.

7. The method of producing a methacrylic acid ester according to claim 1, wherein the conversion of the alcohol or the phenol is within the range of 4-97%.

8. The method of producing a methacrylic acid ester according to claim 2, wherein the conversion of the alcohol or the phenol is within the range of 4-97%.

9. The method of producing a methacrylic acid ester according to claim 1, wherein the reflux ratio is controlled within the range of 5-50.

10. The method of producing a methacrylic acid ester according to claim 2, wherein the reflux ratio is controlled within the range of 5-50.

* * * * *